(12) United States Patent
Papadogianakis et al.

(10) Patent No.: US 8,334,396 B2
(45) Date of Patent: Dec. 18, 2012

(54) PROCESS FOR THE MANUFACTURE OF SATURATED FATTY ACID ESTERS

(75) Inventors: Georgios Papadogianakis, Athens (GR); Achilleas Bouriazos, Peireas (GR); Angeliki Tsichla, Chalandri Athens (GR); Christiana Vasiliou, Nicosia (CY)

(73) Assignee: Cognis IP Management GmbH, Duesseldorf (DE)

( * ) Notice: Subject to any disclaimer, the term of this patent is extended or adjusted under 35 U.S.C. 154(b) by 373 days.

(21) Appl. No.: 12/666,350

(22) PCT Filed: Jun. 14, 2008

(86) PCT No.: PCT/EP2008/004800
§ 371 (c)(1),
(2), (4) Date: Dec. 23, 2009

(87) PCT Pub. No.: WO2009/000435
PCT Pub. Date: Dec. 31, 2008

(65) Prior Publication Data
US 2010/0234625 A1    Sep. 16, 2010

(30) Foreign Application Priority Data

Jun. 23, 2007 (EP) .................................... 07012337

(51) Int. Cl.
*C07C 51/36* (2006.01)
(52) U.S. Cl. ...................................................... 554/141
(58) Field of Classification Search ................... 554/141
See application file for complete search history.

(56) References Cited

FOREIGN PATENT DOCUMENTS

| EP | 0353770 A2 | 2/1990 |
|---|---|---|
| EP | 353770 | * 7/1990 |
| EP | 0435071 B1 | 7/1991 |
| EP | 0435084 A1 | 7/1991 |
| EP | 1918358 A1 | 5/2008 |
| JP | 2000281689 A | 10/2000 |

OTHER PUBLICATIONS

W. Konkol et al. "Herstellung von hydrolytsestabilen Ammoniumsalzen sulfonierter Phosphite and deren Einsatz als Cokatakysatoren in der rhodiumkatalysierten Hydroformylierung" J. prakt. Chem 335 (1993) pp. 75-82.
F. Favre et al. "Hydroformylation of 1-hexene with rhodium in non-aqueous ionic liquids: how to design the solvent and the ligand to the reaction" Chemcomm Communication, 2001 pp. 1360-1361.
A. Piccirilli et al. "Hydrogenation sélective d'esters gras en alcools insaturés en présence de catalyseurs au ruthénium supportés" O.C.L. Oleagineux Corps Gras Lipides, Editions John Libbey Eurotext, Montrouge, FR, vol. 40, No. 9/10 Sep. 1993, pp. 317-322 XP000416256, ISSN: 1258-8210.
H.K.A.C. Coolen et al., "HRh[P(OPh)3]4 as a hydrogenation and isomerization catalyst" Journal of Organo metallic Chemistry 496 (1995) pp. 159-168.
C.H. Chu et al. "Controlling the diffusion of implanted boron in Si and silicide by multiple implants" Materials Chemistry and Physics 54 (1998) pp. 60-66 XP002460163.

* cited by examiner

*Primary Examiner* — Deborah D Carr
(74) *Attorney, Agent, or Firm* — Diehl Servilla LLC

(57) ABSTRACT

Disclosed is a process for the manufacture of saturated fatty acid esters by subjecting unsaturated fatty acid esters to hydrogenation in the presence of a catalyst suitable for catalysing the saturation of double bonds in the esters, which is characterized in that said catalyst represents a homogenous complex of a Group VIII metal and a sulfonated phosphite as the polar ionic ligand.

17 Claims, No Drawings

PROCESS FOR THE MANUFACTURE OF SATURATED FATTY ACID ESTERS

CROSS REFERENCE TO RELATED APPLICATIONS

This application is the National Phase entry of PCT/EP2008/004800, filed Jun. 14, 2008, which claims priority to European patent application number EP07012337.7 filed Jun. 23, 2007, which are incorporated herein by reference in their entireties.

FIELD OF THE INVENTION

The present invention is related to the area of oleochemicals and refers to a process for the manufacture of saturated esters by using a special type of homogenous hydrogenation catalyst.

BACKGROUND OF THE INVENTION

Nowadays, renewable resources are considered to be the new challenge in the development of Sustainable/Green chemistry. Interest in the application of biomass has increased considerably during the last decade because biomass-based resources are renewable and $CO_2$ neutral. In addition, the projected long-term limitations on the exploitation of fossil feedstock, the recent increases in crude oil prices and environmental concerns regarding the local air pollution, the global warming problems caused by $CO_2$, the biodegradability and biocompatibility of many petrochemical based products have also played a role in this respect. Today the world production of renewable biomass is about $200 \cdot 10^9$ t/a of which $130 \cdot 10^6$ t/a are fats and oils and only 7% of the total biomass production capacity are used for food, feed and non-food applications. These figures compared to the world capacity of extracted fossil fuels which is only $7 \cdot 10^9$ t/a show the huge potential of renewable biomass for energy, chemicals and material production. According to the Directive 2003/30/EC of the European Parliament and of the Council by 31 Dec. 2010 biofuels shall be 5.75% of the transportation fuels and according to the US roadmap for biomass technologies—2020 vision goals, biofuels will meet 10% of the fuels, and biomass-based chemicals 18% of the chemicals in the US market.

Vegetable oils and their derivatives are important feedstock for the industry with a broad spectrum of applications such as in foodstuff chemistry, pharmacy, cosmetics, plastics, detergents, biolubricants and in the energy field with the production of biodiesel mainly by transesterification reactions with methanol or ethanol to obtain fatty acid methyl (FAME) or ethyl esters (FAEE).

Catalytic hydrogenation of renewable vegetable oils and their derivatives constitutes a major unit operation in the chemical industry. In such kind of hydrogenation processes of C=C units in unsaturated fatty acids of vegetable oils are commonly used heterogeneous catalytic systems based on nickel, palladium, copper, copper-chromite, platinum etc. However, for edible oil hydrogenation heterogeneous catalysts based on nickel has been the choice of industry. Traditional Ni-based commercial heterogeneous edible oil hydrogenation catalysts produced high amounts in trans-fats (up to 40%). In recent years the negative health effects of trans-fats received increasing attention and decisions have been made in Europe to limit and in USA to declare the trans-isomers contained in fatty foodstuffs which caused a demand for hardstocks with lower trans-isomers content. Therefore, there is increasing interest in the development of new industrial hydrogenation processes producing low amounts of trans-fats. One development may involve the use of homogeneous transition metal complexes as edible oil hydrogenation catalysts. Several attempts have been made to develop homogenous systems which would allow conducting hydrogenation also to saturated compounds under milder conditions in order to improve colour quality of the products and to make the process more economic. Unfortunately, homogenous catalysts based on transition metals modified with conventional phosphites as known from the state of the art suffer from many disadvantages: for example they lack stability against water, they are difficult to remove from the hydrogenation products and/or they simply do not show a sufficient activity.

It has therefore the object of the present invention to overcome the disadvantages known from the state of the art and to provide a cost-effective process for hydrogenation of fatty acid esters which involves a homogenous catalyst system based on transition metals modified with sulfonated phosphites which is stable against hydrolysis, resistant to oxidative destruction, easy to remove from the reaction mixture and exhibiting a high activity.

DETAILED DESCRIPTION OF PREFERRED EMBODIMENTS

The present invention refers to a process for the manufacture of saturated fatty acid esters by subjecting unsaturated fatty acid esters to hydrogenation in the presence of a catalyst suitable for catalysing the saturation of double bonds in the esters, which is characterised in that said catalyst represents a homogenous complex of a Group VIII metal and a sulfonated phosphite as the polar ligand. The process could be also possible to use for the manufacture of partially hydrogenated fatty acid esters which would be valuable products for applications such as "bio-diesel" of improved oxidative stability and cetane number at a low pour point with low NOx emissions, "biolubricants" of higher oxidative stability and a low pour point and "edible oils" of improved oxidative stability and low contents of trans-fats.

Surprisingly it has been observed that homogenous complexes of Group VIII metals comprising polar ligands of the sulfonated phosphite type are more stable in the presence of water compared to conventional phosphites, can be easily separated from the hydrogenation products for example by membrane processes or by phase separation conducting the reaction in an ionic-liquid/organic two-phase system and exhibit an activity which is by far superior compared to other homogenous systems known from the state of the art.

Fatty Acid Esters

Fatty acid esters in the content of this invention shall mean either glycerides or alkyl esters. As far as glycerides are concerned they may represent synthetic or natural mono-, di- or triglyceride or its mixture. Although the nature of the nature, more particular vegetable oils is not critical as long as they include unsaturated fatty acid moieties, the preferred oils are sunflower oil, rape seed oil, linseed oil, olive oil, palm kernel oil, line oil and their mixtures.

Alkyl esters which may also represent suitable starting materials preferably follow general formula (I)

$$R^1CO\text{—}OR^2 \qquad (I)$$

in which $R^1CO$ represents either an unsaturated acyl radical having 16 to 22, preferably 18 carbon atoms or a mixture of saturated and unsaturated acyl radicals having 6 to 22 carbon atoms and a iodine number of at least 5, and $R^2$ stands for a linear or branched alkyl radical having 1 to 6 carbon atoms. Typical examples are methyl or ethyl esters of oleic acid, elaidinic acid, linoleic acid, conjugated linoleic acid, linolenic acid and erucic acid. Also suitable are esters obtained from vegetable oils as described above. The preferred starting material, however, is either a methyl ester of sunflower or palm kernel oil.

In general, said glycerides or esters exhibit a iodine number in the range of 5 to 120, preferably 10 to 100 and more preferably 25 to 95.

Hydrogenation Process

The following Figure shows a simplified pathway of the hydrogenation of C18 compounds in fatty acid methyl esters catalyzed by transition metal trisulfonated triphenylphosphite (TSTPP) complexes in methanol. Methyl α-linolenate (α-MLN), with other C18:3 isomers, are converted to C18:2 isomer mixture and further to C18:1 isomer mixture and finally to the final product methyl stearate (MS). The term "isomer mixture" refers to all regio-isomers obtained from hydrogenation and/or isomerization (along the carbon chain) reactions and all other isomers formed via cis/trans isomerization reactions.

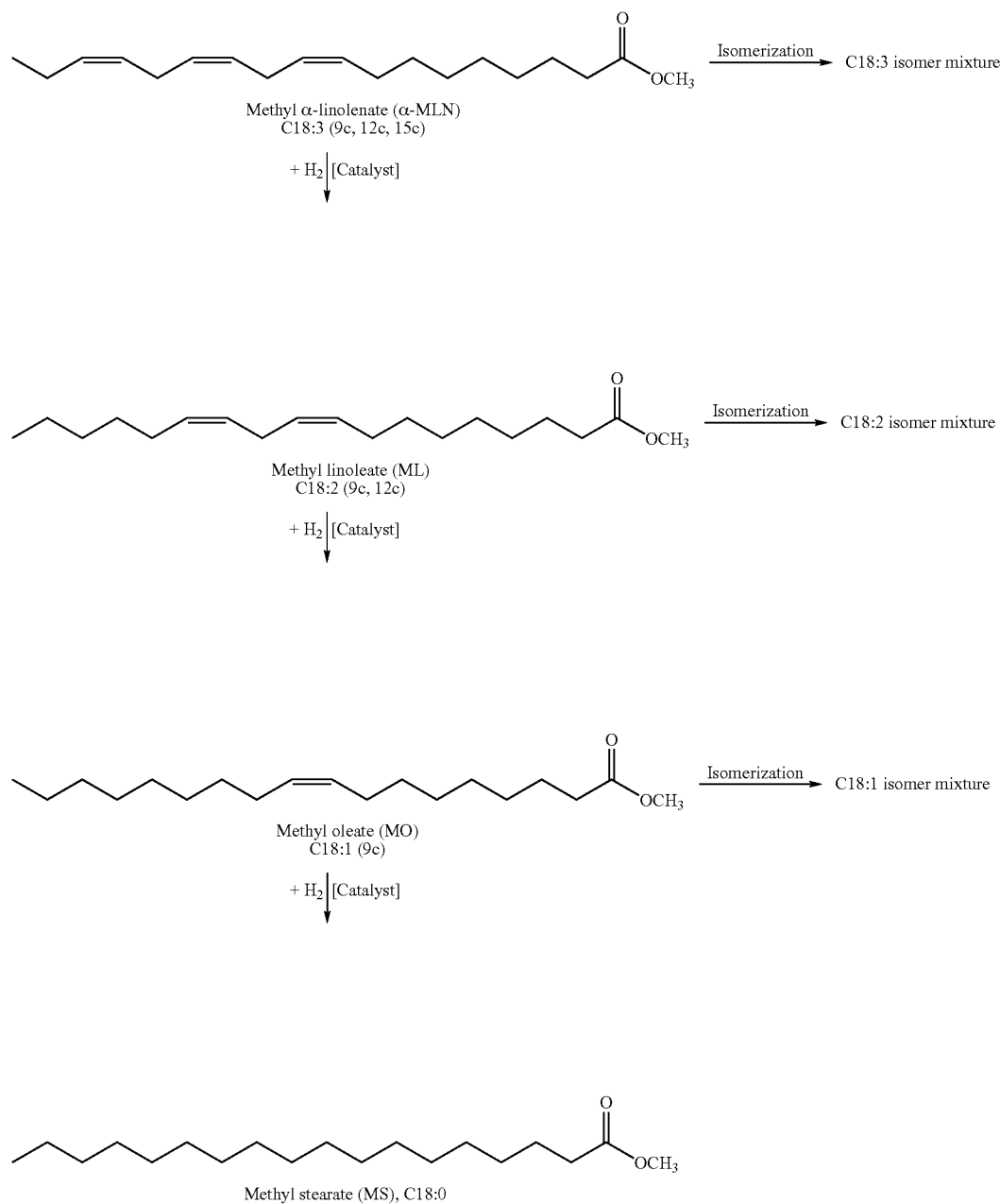

Hydrogenation Catalysts

The homogenous complexes to be used for catalysing the hydrogenation reaction consist of a group VIII metal and a polar ionic ligand system. Preferably said Group VIII metals are selected from the group consisting of rhodium, ruthenium, palladium, cobalt, platinum, nickel, iridium, iron and their mixtures.

The ligands usually follow general formula (II),

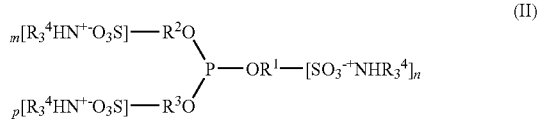

(II)

In which $R^1$, $R^2$ and $R^3$ independently represent a linear or branched $C_1$-$C_{20}$ alkyl or cycloalkyl, a alkylaryl, arylalkyl or aryl radical, preferably a phenyl, benzyl, n-toluoyl, pyridyl, biphenyl, naphthyl or binaphthyl group, $R^4$ stands for an alkyl group having 1 to 12 carbon atoms, and n, m and p represent 0 or integers of from 1 to 3 with the condition than the sum of (n+m+p) is different from zero. Typical examples for suitable sulfonic acid ammonium salts are derived from trialkylphosphites, dialkylarylphosphites, alkyldiarylphosphites or triaryl-phosphites like trimethylphosphite, triethylphosphite, butyldiethylphosphite, tri-n-propylphosphite, tri-n-butylphosphite, tri-2-ethylhexylphosphite, tri-n-octylphosphite, tri-n-dodecylphosphite, dimethylphenylphosphite, Diethylphenylphosphite, methyldiphenyl-phosphite, ethyldiphenylphosphite, triphenylphosphite and trinaphthylphosphite.

The preferred ligands are trisulfonated triphenylphospite (TSTPP) according to general formula (III)

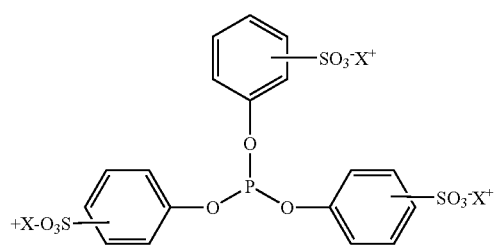

(III)

in which X represents a $R^5N^+R^6R^7R^8$ cation, $R^5$ represents either hydrogen or an alkyl group having 1 to 12, preferably 4 to 8 carbon atoms and $R^6$, $R^7$, $R^8$ represent an alkyl group having 1 to 12, preferably 4 to 8 carbon atoms. The most preferred catalysts represent complexes of Ruthenium or Rhodium with TSTPP. Basically, the molar ratio between the Group VIII metal and the hydrophilic ligand is about 1:1 to about 1:6 and preferably about 1:2 and about 1:4. Overall the content of the Group VIII metal in the reaction mixture is about 10 to about 50 ppm, and preferably about 20 to about 40 ppm. Usually the catalyst amount is adjusted to a molar ratio of C=C/Group VIII metal of about 500 to about 25,000, and preferably 1.000 to 20.000.

Furthermore, suitable polar sulfonated phosphites are given in the following formulas:

Formula (IV):

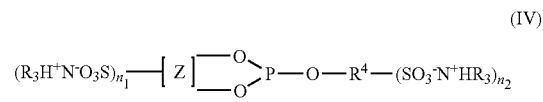

(IV)

In which Z represents an alkyl or aromatic group. The alkyl group stands for a linear or branched $C_1$-$C_{30}$ alkyl or alkyloxyalkyl, alkyl-S-alkyl, or cycloalkyl radical. Aromatic group stands for an aryl, biaryl, naphthyl, binaphthyl, arylalkyl, arylalkylaryl, aryloxyaryl, aryl-S-alkyl, aryl-S-aryl, aryl-N($R^5$)aryl or aryl-N($R^5$)-alkyl moiety in which $R^5$ stands for an alkyl or aromatic radical. $R^4$ represents an alkyl or aromatic group. R of the ammonium moiety stands for an alkyl group having 1 to 12 carbon atoms. $n_1$ and $n_2$ represent 0 or integers of from 1 to 6 with the condition than the sum of ($n_1+n_2$) is different from zero.

Also preferred sulfonated phosphite ligands according to general formula (IV) are:

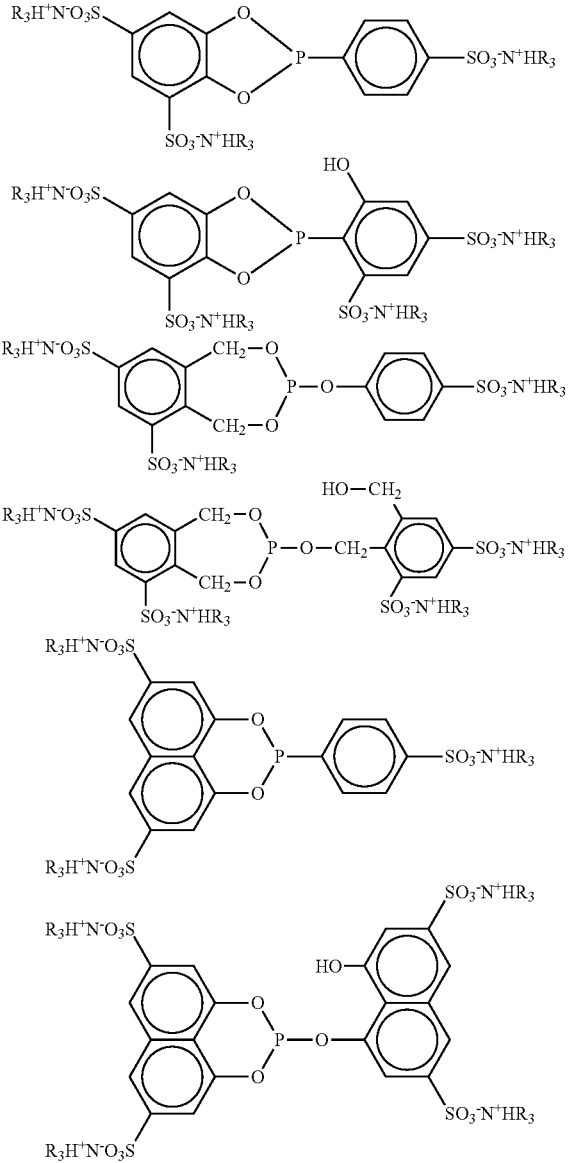

-continued

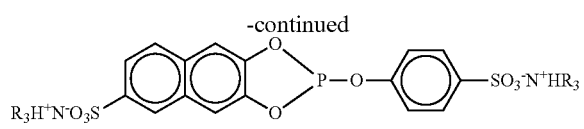
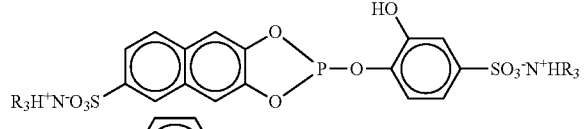
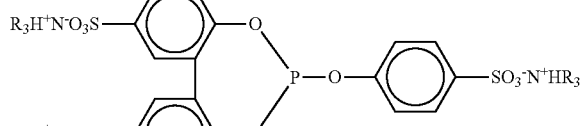
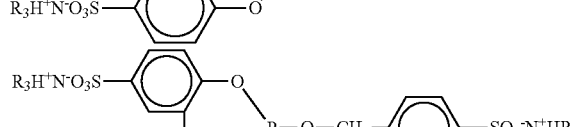
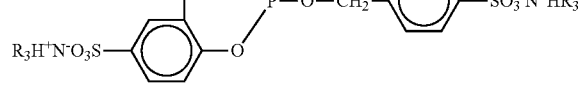
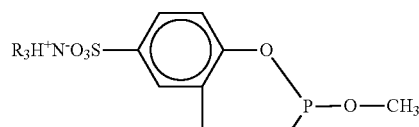
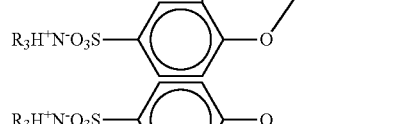
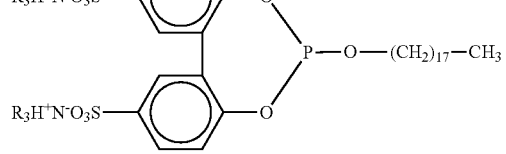
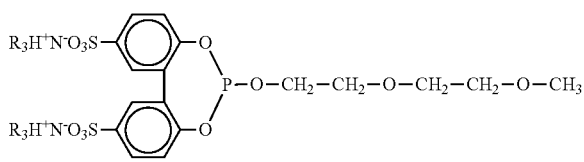
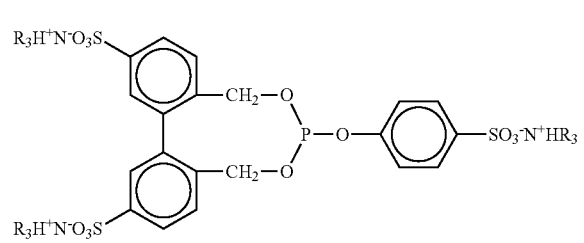
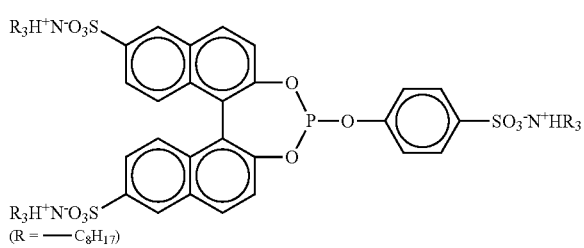

(R = —$C_8H_{17}$)

Formula (V):

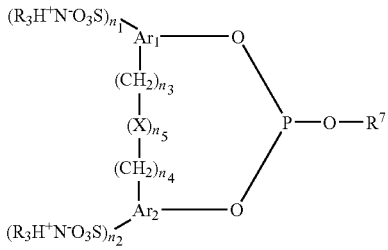

In which $Ar_1$ and $Ar_2$ may be the same or different and represent an arylalkyl, alkylaryl, aryl, biaryl, naphthyl or binaphthyl group. $n_1$ and $n_2$ represent 0 or integers of from 1 to 3 with the condition than the sum of $(n_1+n_2)$ is different from zero. $n_3$, $n_4$ and $n_5$ may be the same or different and represent 0 or 1. X represents a —$CR^8R^9$—, —O—, —S—, —$NR^{10}$—, —$SiR^{11}R^{12}$— and —CO-group. $R^8$ and $R^9$ stand for an H, $C_1$-$C_{12}$-alkyl, phenyl, toluoyl and anisol group. $R^{10}$ and $R^{12}$ stands for a H or methyl group. $R^7$ stands for an $C_1$-$C_{12}$-alkyl, alkylaryl, arylalkyl, cyclo-hexyl, 1-methylcyclohexyl- and a benzyl group. The preferred sulfonated phosphite ligands according to general formula (V) are:

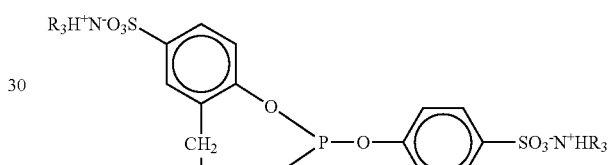

Formula (VI):

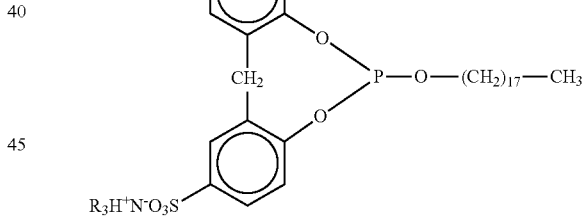

In which Z represents an alkyl or aromatic group. The alkyl group stands for a linear or branched $C_1$-$C_{30}$ alkyl or alkyloxyalkyl, alkyl-S-alkyl, or cycloalkyl radical. Aromatic group stands for an aryl, biaryl, naphthyl, binaphthyl, arylalkyl, arylalkylaryl, aryloxyaryl, aryloxyalkyl, aryl-S-alkyl, aryl-S-aryl, aryl-N($R^5$)aryl or aryl-N($R^5$)-alkyl moiety in which $R^5$ stands for an alkyl or aromatic radical. $n_1$, $n_2$ and $n_3$ represent 0 or integers of from 1 to 3 with the condition than the sum of $(n_1+n_2+n_3)$ is different from zero. The preferred sulfonated phosphite ligands according to general formula (VI) are:

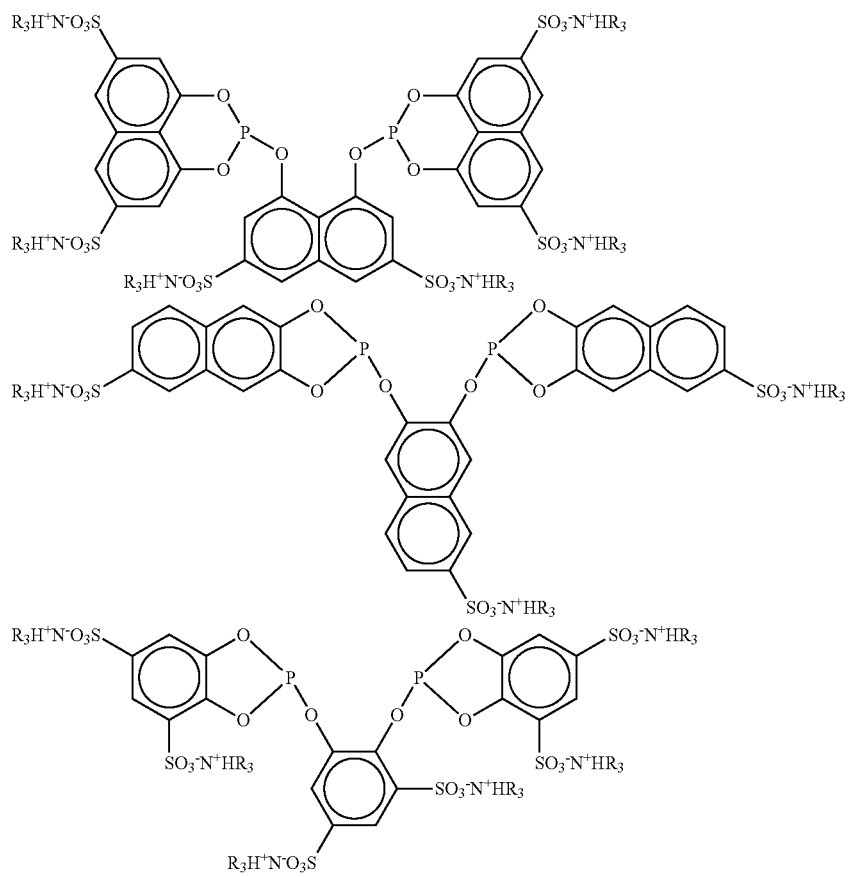
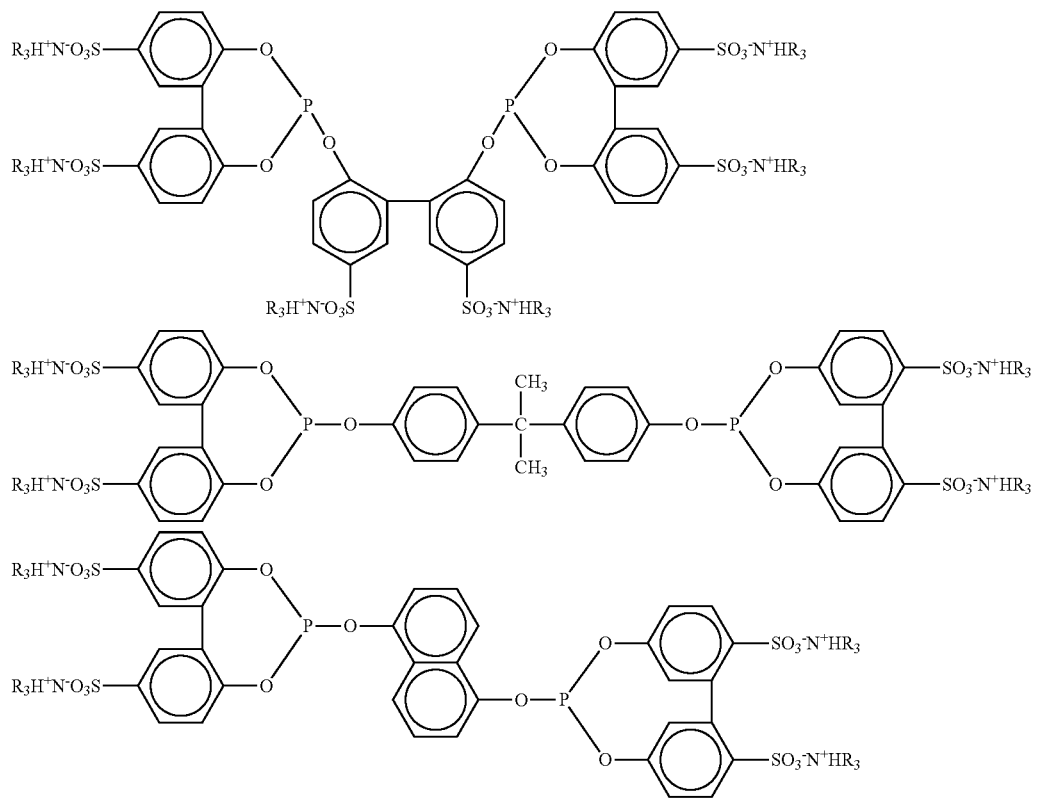

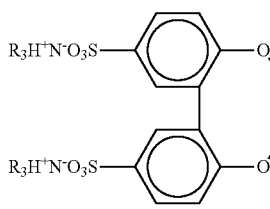 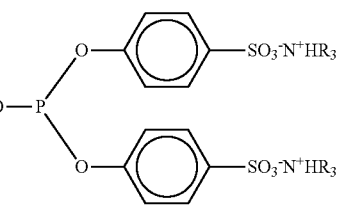

-continued

The catalysts described above are known from the prior art and disclosed in EP 0435071 B1 and EP 0435084 B1 according to which a sulfonic acid was reacted with the amine and subjected to transesterification with the phosphite compound. According to JP 2000 281689 A1 (Mitsubishi) a sulfonic acid metal salt is reacted with an ammoniumchloride of the amine and then transesterified with a phosphite. Also references are made to J. Prakt. Chem./Chem. Ztg. 335, 75ff (1993) which describes the use of said systems for the monophasic hydroformylation of α-olefins in organic solvents and to Chem. Commun. (2001) 1360 which describes the use of said systems for the biphasic hydroformylation of α-olefines in ionic liquids based on imidazolium cations where the catalyst was easily separated by simple phase separation from organic products and recycled without loss of its high selectivity toward linear aldehydes. As far as the synthesis of TSTPP and the complexes is concerned the teaching of the aforementioned documents is fully incorporated by reference.

Hydrogenation Process

In order to avoid ambiguities about the meaning of the phrase "hydrogenation" it is pointed out that this phrase refers to the saturation of the double bonds only and is equivalent to the phrase "hardening".

In a preferred embodiment of the process according to the present invention hydrogenation is conducted in the presence of a solvent. Suitable solvents are selected from lower alcohols or dialkyl ethers, like for example methanol, ethanol, butanol and diethyl ether.

Usually, the mixture comprising the ester or glyceride, the catalyst and optionally the organic solvent is transferred into a stirred autoclave purged with argon and after a number of pressurising-depressurising cycles with hydrogen in order to remove all traces of oxygen. Then the reactor is heated up to about 50 to about 120, preferably about 80 to about 100° C. and kept there for a reaction time of about 5 to about 240, preferably about 10 to about 60 minutes. During this time the pressure rises up to about 5 to about 100 bar. Once the reaction has been completed the mixtures is cooled to room temperature and depressurised. The catalyst can be removed and recovered on a quantitative basis by means of a membrane. In the case that the hydrogenation reaction is performed in an ionic-liquid/organic two-phase system the catalyst is removed and recovered on a quantitative basis by a simple phase separation.

INDUSTRIAL APPLICATION

The homogenous complexes to be used according to the process of the present invention show a high activity in catalysing the hydrogenation of unsaturated materials, which is not limited to fatty acid esters, but could be also of value for producing paraffins from olefins and the like. Another object of the present invention is therefore directed to the use of complexes of a Group VIII metal and a sulfonated phosphite as the polar ionic ligand as homogenous catalysts for the hydrogenation of double bonds in general and in particular for the hydrogenation of unsaturated fatty acid esters in organic monophasic or ionic-liquids/organic two-phase systems.

EXAMPLES

Examples 1 to 10

Hydrogenation of $C_{12}$-$C_{18}$ Palm Kernel Methyl Ester

The following examples describe the hydrogenation of palm kernel methyl ester (Edenor® PK 12-18 ME, Cognis GmbH) in the presence of homogenous trisulfonated triphenylphospite (TSTPP) Rhodium- or Ruthenium complexes as catalysts. The following reaction conditions were applied:
Hydrogenation time: 60 min,
1.32 mg (0.005 mmol) $RhCl_3 \cdot 3H_2O$ except in entries 1-3 when added 1.31 mg (0.005 mmol) $RuCl_3 \cdot 3H_2O$, 28.01 mg (0.02 mmol) TSTPP (P/Rh molar ratio=4), 20 ml methanol, [Rh]=28 ppm except in entries 1 and 2 when was [Ru]=24 ppm and in entry 3 when was [Ru]=26 ppm.
Stirring rate=850 rpm.
Additional details of the hydrogenation and the results of the trials are compiled in Table 1.

TABLE 1

Hydrogenation of $C_{12}$-$C_{18}$ palm kernel methyl ester[a]

| Ex. | C=C/Rh molar ratio | T °C. | $P_{H2}$ bar | C18:2 total mol % | C18:1 total mol % | cis-C18:1 total mol % | trans-C18:1 total mol % | C18:0 mol % |
|---|---|---|---|---|---|---|---|---|
| Edenor[a] | — | — | — | 9.9[a] | 83.0[a] | 83.0[a] | — | 7.1 |
| 1 | 500 | 100 | 80 | 2.3 | 61.4 | 40.4 | 21.0 | 36.3 |
| 2 | 500 | 100 | 100 | 2.5 | 62.1 | 42.7 | 19.4 | 35.4 |
| 3 | 300 | 100 | 80 | 2.0 | 52.2 | 39.7 | 12.5 | 45.8 |
| 4 | 300 | 100 | 80 | 0.0 | 24.0 | 1.8 | 22.2 | 76.0 |
| 5 | 300 | 110 | 80 | 0.5 | 35.9 | 4.7 | 31.2 | 63.6 |
| 6 | 300 | 90 | 80 | 0.4 | 17.9 | 1.3 | 16.6 | 81.7 |
| 7 | 300 | 80 | 80 | 0.5 | 3.7 | 0.0 | 3.7 | 95.8 |
| 8 | 300 | 70 | 80 | 0.5 | 13.5 | 0.1 | 13.4 | 86.0 |

TABLE 1-continued

Hydrogenation of $C_{12}$-$C_{18}$ palm kernel methyl ester[a]

| Ex. | C=C/Rh molar ratio | T °C. | $P_{H2}$ bar | C18:2 total mol % | C18:1 total mol % | cis-C18:1 total mol % | trans-C18:1 total mol % | C18:0 mol % |
|---|---|---|---|---|---|---|---|---|
| 9 | 300 | 80 | 100 | 0.6 | 15.7 | 0.0 | 15.7 | 83.7 |
| 10 | 300 | 80 | 50 | 0.5 | 15.4 | 0.2 | 15.2 | 84.1 |

[a] Edenor ME PK 12-18 F of Cognis except the C18 compounds (14.1 mol %) further contains: 0.8 mol % methyl decanoate (C10:0), 57.1 mol % methyl dodecanoate (C12:0), 18.7 mol % methyl tetradecanoate (C14:0) and 9.3 mol % methyl palmitate (MP, C16:0) which were ignored in the experiments. The C18 total content of 14.1 mol % with the proportion of 1.0 mol % methyl stearate (C18:0), 11.7 mol % methyl oleate (C18:1) and 1.4 mol % methyl linoleate (C18:2) was calculated to 100 mol % to give 7.1 mol % of C18:0, 83.0 mol % of C18:1 and 9.9 mol % of C18:2.

Examples 11-32

Hydrogenation of Sunflower Methyl Ester

The following examples describe the hydrogenation of sunflower methyl ester in the presence of homogenous trisulfonated triphenylphospite (TSTPP) Rhodium-, Ruthenium-, Iridium- or Palladium complexes as catalysts. The following reaction conditions were applied:

Reaction time: 60 min; except entries 30 and 31, t=20 min; entry 32, t=30 min;

1.32 mg (0.005 mmol) $RhCl_3 \cdot 3H_2O$; except entries 23-25, 1.76 mg (0.005 mmol) $IrCl_3 \cdot 3H_2O$; except entries 26, 27 and 30, 1.31 mg (0.005 mmol) $RuCl_3 \cdot 3H_2O$; except entry 28, 0.89 mg (0.005 mmol) $PdCl_2$ and entry 29, 1.12 mg (0.005 mmol) $Pd(OAc)_2$.

Stirring rate: 850 rpm.

Additional details of the hydrogenation and the results of the trials are compiled in Table 2.

TABLE 2

Hydrogenation of sunflower methyl ester[d]

| Ex. | Catalyst Precursor | C=C/M molar ratio | L/M molar ratio | T ° C. | $P_{H2}$ bar | Solvent | C18:3 total mol % | C18:2 total mol % | C18:1 total mol % | cis-C18:1 total mol % | trans-C18:1 total mol % | C18:0 mol % |
|---|---|---|---|---|---|---|---|---|---|---|---|---|
| Ester[d] | — | — | — | — | — | — | 1.2[e] | 63.3[f] | 32.0[g] | 32.0[g] | — | 3.5 |
| 11 | $RhCl_3 \cdot 3H_2O$/TSTPP | 500 | 3 | 110 | 50 | MeOH | 0.6 | 0.0 | 22.0 | 2.0 | 20.0 | 77.4 |
| 12 | $RhCl_3 \cdot 3H_2O$/TSTPP | 500 | 4 | 110 | 50 | MeOH | 0.6 | 0.0 | 19.4 | 1.8 | 17.6 | 80.0 |
| 13 | $RhCl_3 \cdot 3H_2O$/TSTPP | 500 | 5 | 110 | 50 | MeOH | 0.0 | 10.6 | 65.6 | 26.8 | 38.8 | 23.8 |
| 14 | $RhCl_3 \cdot 3H_2O$/TSTPP | 500 | 4 | 110 | 80 | MeOH | 0.8 | 7.7 | 58.0 | 14.5 | 43.5 | 33.5 |
| 15 | $RhCl_3 \cdot 3H_2O$/TSTPP | 500 | 4 | 110 | 30 | MeOH | 0.1 | 4.8 | 57.7 | 12.9 | 44.8 | 37.4 |
| 16 | $RhCl_3 \cdot 3H_2O$/TSTPP | 500 | 4 | 100 | 50 | MeOH | 1.0 | 0.0 | 12.0 | 0.5 | 11.5 | 87.0 |
| 17 | $RhCl_3 \cdot 3H_2O$/TSTPP | 500 | 4 | 90 | 50 | MeOH | 1.1 | 13.2 | 58.6 | 24.4 | 34.2 | 27.1 |
| 18 | $RhCl_3 \cdot 3H_2O$/TSTPP | 500 | 4 | 100 | 50 | — | 1.5 | 58.8 | 33.3 | 31.8 | 1.5 | 6.4 |
| 19 | $RhCl_3 \cdot 3H_2O$/TSTPP | 500 | 4 | 100 | 50 | Ether | 0.0 | 62.3 | 33.0 | 33.0 | 0.0 | 4.7 |
| 20 | $RhCl_3 \cdot 3H_2O$/TSTPP | 500 | 4 | 100 | 50 | MeOAc | 1.6 | 59.6 | 33.3 | 32.6 | 0.7 | 5.5 |
| 21 | $RhCl_3 \cdot 3H_2O$/$PPh_3$ | 500 | 4 | 100 | 50 | MeOH | 1.0 | 4.4 | 51.4 | 16.3 | 35.1 | 43.2 |
| 22 | $RhCl_3 \cdot 3H_2O$/$P(OPh)_3$ | 500 | 4 | 100 | 50 | MeOH | 2.4 | 8.8 | 60.8 | 31.5 | 29.3 | 28.0 |
| 23[h] | $IrCl_3 \cdot 3H_2O$/TSTPP | 500 | 4 | 100 | 30 | MeOH | 6.4 | 9.0 | 46.5 | 15.6 | 30.9 | 21.8 |
| 24[i] | $IrCl_3 \cdot 3H_2O$/TSTPP | 500 | 4 | 100 | 50 | MeOH | 2.6 | 3.6 | 42.0 | 7.2 | 34.8 | 43.3 |
| 25[j] | $IrCl_3 \cdot 3H_2O$/STPP | 500 | 4 | 100 | 80 | MeOH | 1.9 | 1.8 | 38.0 | 4.9 | 33.1 | 50.1 |
| 26 | $RuCl_3 \cdot 3H_2O$/TSTPP | 500 | 4 | 100 | 50 | MeOH | 0.0 | 3.0 | 44.4 | 22.8 | 21.6 | 52.6 |
| 27 | $RuCl_3 \cdot 3H_2O$/TSTPP | 500 | 4 | 100 | 80 | MeOH | 0.0 | 0.6 | 10.2 | 0.0 | 10.2 | 89.2 |
| 28 | $PdCl_2$/TSTPP | 500 | 4 | 100 | 50 | MeOH | 1.1 | 17.3 | 70.9 | 53.2 | 17.7 | 10.7 |
| 29 | $Pd(OAc)_2$/TSTPP | 500 | 4 | 100 | 50 | MeOH | 0.7 | 25.4 | 66.5 | 48.5 | 18.0 | 7.4 |
| 30 | $RuCl_3 \cdot 3H_2O$/TSTPP | 500 | 4 | 100 | 80 | MeOH | 2.4 | 20.9 | 49.0 | 41.4 | 7.6 | 27.7 |
| 31 | $RhCl_3 \cdot 3H_2O$/TSTPP | 500 | 4 | 100 | 50 | MeOH | 1.2 | 16.3 | 60.3 | 31.9 | 28.7 | 21.9 |

TABLE 2-continued

Hydrogenation of sunflower methyl ester[d]

| Ex. | Catalyst Precursor | C=C/M molar ratio | L/M molar ratio | T °C. | $P_{H2}$ bar | Solvent | C18:3 total mol % | C18:2 total mol % | C18:1 total mol % | cis-C18:1 total mol % | trans-C18:1 total mol % | C18:0 mol % |
|---|---|---|---|---|---|---|---|---|---|---|---|---|
| 32 | RhCl$_3$•3H$_2$O/ TSTPP | 500 | 4 | 100 | 50 | MeOH | 0.0 | 8.5 | 61.6 | 20.6 | 41.0 | 29.9 |

[d]Sunflower Fatty Acid ME of Cognis except the C18 compounds with a total content of 94.1 mol % further contains 5.3 mol % methyl palmitate (MP, C16:0) and 0.6 mol % of methyl docosanate (MD, C22:0) which were ignored in the experiments. The C18 total content of 94.1 mol % with the proportion of 1.1 mol % methyl linolenate (C18:3), 59.6 mol % methyl linoleate (C18:2), 30.1 mol % methyl oleate (C18:1) and 3.3 mol % methyl stearate (C18:0) was calculated to 100 mol % to give 1.2 mol % of C18:3, 63.3 mol % C18:2, 32.0 mol % C18:1 and 3.5 mol % C18:0.
[e]Methyl α-linolenate (α-MLN), C18:3 (9c, 12c, 15c).
[f]Methyl linoleate (ML), C18:2 (9c, 12c).
[g]Methyl oleate (MO), C18:1 (9c).
[h]16.3 mol % from three unidentified products
[i]8.5 mol % from three unidentified products
[j]8.2 mol % from three unidentified products

What is claimed is:

1. A process for the manufacture of saturated fatty acid esters comprising subjecting unsaturated fatty acid esters to hydrogenation in the presence of a catalyst suitable for catalysing the saturation of double bonds in the esters, wherein said catalyst is selected from rhodium and/or ruthenium, with at least one polar ionic ligand that is trisulfonated triphenyl phosphite (TSTPP).

2. The process of claim 1, wherein said ester is selected from the group consisting of glycerides and alkyl esters.

3. The process of claim 2, wherein said glyceride is selected from the group consisting of synthetic or natural monoglycerides, diglycerides, triglycerides and combinations thereof.

4. The process of claim 2, wherein said glyceride is selected from the group consisting of sunflower oil, rape seed oil, olive oil, palm kernel oil, linseed oil and combinations thereof.

5. The process of claim 2, wherein said ester is represented by formula (I)

$$R^1CO-OR^2 \qquad (I)$$

in which $R^1CO$ represents either an unsaturated acyl moiety having 16 to 22 carbon atoms, or a mixture of saturated and unsaturated acyl moieties having 6 to 22 carbon atoms, and having an iodine number of at least 5; and $R^2$ stands for a linear or branched alkyl group having 1 to 6 carbon atoms.

6. The process of claim 5, wherein said ester comprises the methyl ester of sunflower and/or palm kernel oil.

7. The process of claim 2, wherein said glycerides or esters exhibit an iodine value in the range of 5 to 127.

8. The process of claim 1, wherein the molar ratio between the rhodium and/or ruthenium and the trisulfonated triphenyl phosphite (TSTPP) is about 1:1 to about 1:100.

9. The process of claim 1, wherein the content of the rhodium and/or ruthenium in the reaction mixture is about 10 to about 1000 ppm.

10. The process of claim 1, wherein the molar ratio of C=C/rhodium and/or ruthenium is about 200 to about 50,000.

11. The process of claim 1, wherein hydrogenation is conducted in the presence of a solvent.

12. The process of claim 11, wherein said solvent comprises a lower alcohol or a dialkyl ether.

13. The process of claim 1, wherein the hydrogenation is conducted at a temperature within the range of about 50 to about 120° C.

14. The process of claim 1, wherein the hydrogenation is conducted under a pressure in the range of about 5 to about 100 bar.

15. The process of claim 1, wherein the hydrogenation is conducted over a reaction time of about 5 to about 240 minutes.

16. A method for the hydrogenation of double bonds comprising adding at least one complex of rhodium and/or ruthenium and trisulfonated triphenyl phosphite (TSTPP) as a polar ionic ligand, as a homogenous catalyst, to a hydrogenation reaction mixture, and submitting the resulting mixture to hydrogenation conditions.

17. A method for the hydrogenation of unsaturated fatty acid esters comprising adding at least one complex of rhodium and/or ruthenium and TSTPP to a hydrogenation reaction mixture, and submitting the resulting mixture to hydrogenations conditions.

\* \* \* \* \*